US 9,974,448 B2

(12) United States Patent
Mills et al.

(10) Patent No.: US 9,974,448 B2
(45) Date of Patent: May 22, 2018

(54) HEMODYNAMIC MONITORING

(71) Applicants: LiDCO Group PLC, London (GB); CNSystems Medizintechnik AG, Graz (AT)

(72) Inventors: Eric Mills, London (GB); Terence Kevin O'Brien, Cambridge (GB); Jürgen Fortin, Graz (AT); Katja Maier, Graz (AT)

(73) Assignees: CNSystems Medizintechnik AG, Graz (AT); LiDCO Group PLC, London (GB)

( * ) Notice: Subject to any disclaimer, the term of this patent is extended or adjusted under 35 U.S.C. 154(b) by 0 days. days.

(21) Appl. No.: 14/834,676

(22) Filed: Aug. 25, 2015

(65) Prior Publication Data
US 2015/0359435 A1  Dec. 17, 2015

Related U.S. Application Data

(63) Continuation of application No. 13/664,670, filed on Oct. 31, 2012.

(51) Int. Cl.
*A61B 5/02* (2006.01)
*A61B 5/022* (2006.01)
*A61B 5/00* (2006.01)
*A61B 5/0225* (2006.01)

(52) U.S. Cl.
CPC ............ *A61B 5/022* (2013.01); *A61B 5/0225* (2013.01); *A61B 5/6824* (2013.01); *A61B 5/6826* (2013.01); *A61B 2560/0223* (2013.01)

(58) Field of Classification Search
None
See application file for complete search history.

(56) References Cited

U.S. PATENT DOCUMENTS

| | | | |
|---|---|---|---|
| 5,014,714 A | * | 5/1991 | Millay ............... A61B 5/02225 600/485 |
| 5,785,659 A | | 7/1998 | Caro et al. |

(Continued)

FOREIGN PATENT DOCUMENTS

| | | |
|---|---|---|
| CN | 201658367 U | 12/2010 |
| CN | 102551693 A | 7/2012 |

(Continued)

OTHER PUBLICATIONS

International Search Report and Written Opinion dated Feb. 5, 2014, which issued in corresponding International Patent Application No. PCT/GB2013/052799 (9 pages).

(Continued)

*Primary Examiner* — Etsub Berhanu
(74) *Attorney, Agent, or Firm* — Nixon Peabody LLP

(57) ABSTRACT

A device and method for use in monitoring blood pressure. The device comprises a controller configured to monitor a first blood pressure measurement based on a first blood pressure signal. The controller is configured to initiate acquiring a second blood pressure measurement based on a second blood pressure signal if the first blood pressure measurement exceeds a predetermined threshold. The decision to initiate acquiring the second blood pressure measurement is based on only one blood pressure measurement.

9 Claims, 3 Drawing Sheets

(56) References Cited

U.S. PATENT DOCUMENTS

| | | | | |
|---|---|---|---|---|
| 2010/0081945 A1* | 4/2010 | Sethi | ................. | A61B 5/02007 600/485 |
| 2011/0021929 A1 | 1/2011 | Sethi et al. | | |
| 2011/0118618 A1* | 5/2011 | John | .................... | A61B 5/0476 600/544 |
| 2011/0257539 A1* | 10/2011 | Sawanoi | ................ | G01G 23/16 600/493 |

FOREIGN PATENT DOCUMENTS

| | | |
|---|---|---|
| JP | 03218728 A2 | 9/1991 |
| JP | 08187227 A2 | 7/1996 |
| JP | 2000157501 A2 | 6/2000 |
| JP | 2011050438 A2 | 3/2011 |
| WO | 2005/018444 A1 | 3/2005 |

OTHER PUBLICATIONS

United Kingdom Search and Examination Report corresponding to co-pending United Kingdom Patent Application Serial No. GB 1219871.9, United Kingdom Intellectual Patent Office, dated Mar. 5, 2013 (7 pages).

NHS Choices Website; High Blood Pressure (Hypertension)—Diagnosis; dated Apr. 23, 2012 (2 pages).

\* cited by examiner

HEMODYNAMIC MONITORING

CROSS-REFERENCE TO RELATED APPLICATIONS

This application is a Continuation of U.S. patent application Ser. No. 13/664,670, filed Oct. 31, 2012, which is incorporated herein by reference in its entirety

COPYRIGHT

A portion of the disclosure of this patent document contains material which is subject to copyright protection. The copyright owner has no objection to the facsimile reproduction by anyone of the patent disclosure, as it appears in the Patent and Trademark Office patent files or records, but otherwise reserves all copyright rights whatsoever.

FIELD OF THE INVENTION

The invention relates generally to a device and method suitable for use in monitoring blood pressure.

BACKGROUND

In medicine it is often desirable to monitor blood pressure, for example, over the course of an invasive procedure. Blood pressure is most reliably measured using an arterial line. The fitting of an arterial line is invasive and is most commonly performed under anaesthetic.

Ways and means of measuring blood pressure non-invasively are also known. The most common method of measuring blood pressure non-invasively is via an inflatable cuff placed around the upper arm. Whilst accurate, these measurements obstruct blood flow to the limb and therefore may only be taken intermittently.

Alternative methods of measuring blood pressure that maintain the blood flow through the interrogated artery are known. The "vascular unloading technique," as described in U.S. patents U.S. Pat. No. 6,669,648, U.S. Pat. No. 7,390,301 and U.S. Pat. No. 8,114,025 and US patent applications US 2011/0105917 and US 2011/0105918, continuously measures the blood pressure through an inflatable cuff fitted to a finger. This known method allows blood flow to be maintained through the interrogated artery thus making long term continuous measurement possible. The pressure load on and blood congestion in the interrogated artery is limited by providing a second finger cuff on a second finger and alternating between the two cuffs when taking blood pressure measurements.

It will be appreciated that it may not be possible to directly compare blood pressure measurements taken with different measurement techniques or on different points of the body, not least due to the difference in blood pressure between the smaller arteries, for example in a finger, and the major arteries. For this reason it may be beneficial to calibrate blood pressure measurements.

SUMMARY OF INVENTION

According to an embodiment of the invention there is provided a device for use in monitoring blood pressure comprising a controller configured to monitor a first blood pressure measurement based on a first blood pressure signal. The controller is further configured to initiate acquiring a second blood pressure measurement based on a second blood pressure signal if the first blood pressure measurement exceeds a predetermined threshold. The decision to initiate acquiring the second blood pressure measurement is based on only one blood pressure measurement, such as the first blood pressure measurement. By focussing the monitoring of the blood pressure measurement on a single measurement discomfort to the patient is further reduced.

According to a second embodiment of the invention there is provided a method of monitoring blood pressure comprising receiving a first blood pressure signal, monitoring a first blood pressure measurement based on the first blood pressure signal and initiating acquiring a second blood pressure measurement based on a second blood pressure signal if the first blood pressure measurement exceeds a predetermined threshold. The decision to initiate acquiring the second blood pressure measurement is based on only one blood pressure measurement.

The predetermined threshold may be a minimum or maximum threshold. The first blood pressure signal may be a continuous and/or non-invasive blood pressure signal, such as that provided from a single finger cuff (such as one of the finger cuffs described in the above U.S. patent, for example). The second blood pressure signal may be provided by or obtained from/through measurement equipment/ spygmamometer using an inflatable arm cuff.

The device for use in monitoring blood pressure may itself comprise some or all pressure cuffs or other devices needed for acquiring the first and/or second blood pressure signals. The device may thus further comprise an arm cuff and/or a finger cuff. Alternatively, the device may simply be a monitoring and control unit that receives blood pressure signals from known blood pressure measurement devices already in clinical use. The device may be form part of a haemodynamic monitor.

In monitoring the first blood pressure measurement the controller can determine when it is desirable (in keeping with the above discussed threshold) for the calibration of the first blood pressure measurement to be checked. By only initiating a calibration measurement when the blood pressure measurement exceeds a predetermined threshold the number of calibration measurements are minimised. This is advantageous as a large amount of secondary calibration measurements may cause the subject discomfort and may temporarily interfere with the first blood pressure measurement.

The controller may be configured to base the decision to initiate acquiring the second blood pressure measurement on pulse pressure calculated using the first blood pressure signal. The pulse pressure (PP) is the difference between the systolic ($P_{sys}$) and diastolic ($P_{dia}$) pressures, that is:

$$PP = P_{sys} - P_{dia}$$

The controller may initiate acquiring the second blood pressure measurement if the pulse pressure exceeds a predetermined threshold. Pulse pressure usually stays within a certain range. A healthy resting pulse pressure for a normal adult is around 30-40 mmHG. If very high or very low pulse pressures are measured then such values can be taken as an indication that the calibration of the first blood pressure measurement may require checking. In one embodiment the controller is configured to initiate acquiring the second blood pressure measurement if the pulse pressure falls below 15 mmHG and/or if the pulse pressure exceeds 150 mmHG.

Additionally or alternatively a large change in pulse pressure occurring over a short time may be an indication that the calibration of a blood pressure measurement should be checked. The controller may be configured to initiate acquiring the second blood pressure measurement if the change in pulse pressure over a period of time exceeds a predetermined threshold. The period of time may be a fixed time period, such as over the preceding 90 seconds. In one embodiment the controller is configured to initiate acquiring the second blood pressure measurement if the pulse pressure decreases by more than 50% within 90 seconds and/or if the pulse pressure increases by more than 100% within 90 seconds.

Alternatively or additionally changes in pulse pressure can be monitored over a period of time that has started at a fixed point in time. The controller may, for example, be configured to initiate acquiring the second blood pressure measurement if the pulse pressure changes by a predetermined amount since the last previous acquisition of the second blood pressure signal. An increase in pulse pressure by more than 60% since a previous second blood pressure measurement and/or a decrease in pulse pressure by more than 150% since a previous second blood pressure measurement have been particularly found to be indicative of a situation where a check of the calibration of the blood pressure measurement is desirable. Such large variations in pulse pressure over a short period of time are not normally encountered as a result of physiological or pathological events and can therefore be good indicators that the calibration of the first blood pressure signal may require checking.

A further parameter that has been found to be a good indicator that a calibration check may be required is the med-dia ratio. The med-dia ratio is the difference between the mean arterial pressure (MAP) and the diastolic pressure ($P_{dia}$) divided by the pulse pressure (PP), i.e.:

$$MD = \frac{MAP - P_{dia}}{P_{sys} - P_{dia}}$$

The controller may be configured to initiate acquiring a second blood pressure measurement based on med-dia-ratio calculated based on the first blood pressure signal. The controller may be configured to initiate acquiring the second blood pressure measurement if the med-dia-ratio exceeds a predetermined threshold. In one embodiment, the controller is configured to initiate acquiring the second blood pressure measurement if the med-dia-ratio falls below 21% and/or exceeds 51%.

Once the second blood pressure measurement has been received/acquired, the first blood pressure measurement may be re-calibrated based on the second blood pressure measurement. Calibrating the first blood pressure measurement may involve amplifying it or adding a bias to it so that certain values closely match those of the second blood pressure measurement. On the other hand, if the first and second blood pressure measurements do not differ significantly, then the first blood pressure measurement may simply be retained as accurate and recalibration may not be performed. The controller may be configured to calibrate the first blood pressure measurement based on the second blood pressure measurement if it differs from the second blood pressure measurement by a predetermined amount. The controller may, for example be configured/programmed to compare the systolic blood pressure values of the first and second blood pressure measurements or the diastolic blood pressure values of these two measurements, or both. It was found that, if the first and second blood pressure measurements differ by 13 mmHG or less re-calibration can be omitted and the controller maybe configured accordingly.

Where a calibration check has not resulted in recalibration, i.e. where a difference between the first and second blood pressure measurements was deemed too small to warrant re-calibrating the first blood pressure measurement, it may be advantageous to temporarily inhibit automatic recalibration checks to prevent the device from repeatedly rechecking measurements that are known to be accurately calibrated. In one embodiment, the controller is configured to inhibit any steps of initiating acquisition of a second blood pressure measurement if a second blood pressure measurement has been taken during a predetermined preceding period of time and the first blood pressure measurement was not re-calibrated. The decision to inhibit initiating the acquisition of a second blood pressure signal may be applied by the controller so that none of a plurality of thresholds is used for assessing the need for acquiring a second blood pressure signal in the predetermined period of time.

The controller may also configured to not initiate acquiring a second blood pressure measurement based on a specific predetermined threshold being exceeded, if, during a predetermined preceding period of time, a second blood pressure measurement has been taken based on said predetermined threshold being exceeded and the first blood pressure measurement was not recalibrated. This is particularly advantageous for absolute value thresholds, such as maximum and minimum pulse pressure or med-dia-ratio.

BRIEF DESCRIPTION OF THE DRAWINGS

The present invention will be understood and appreciated more fully from the following detailed description taken in conjunction with drawings in which.

DETAILED DESCRIPTION

Figure 1:
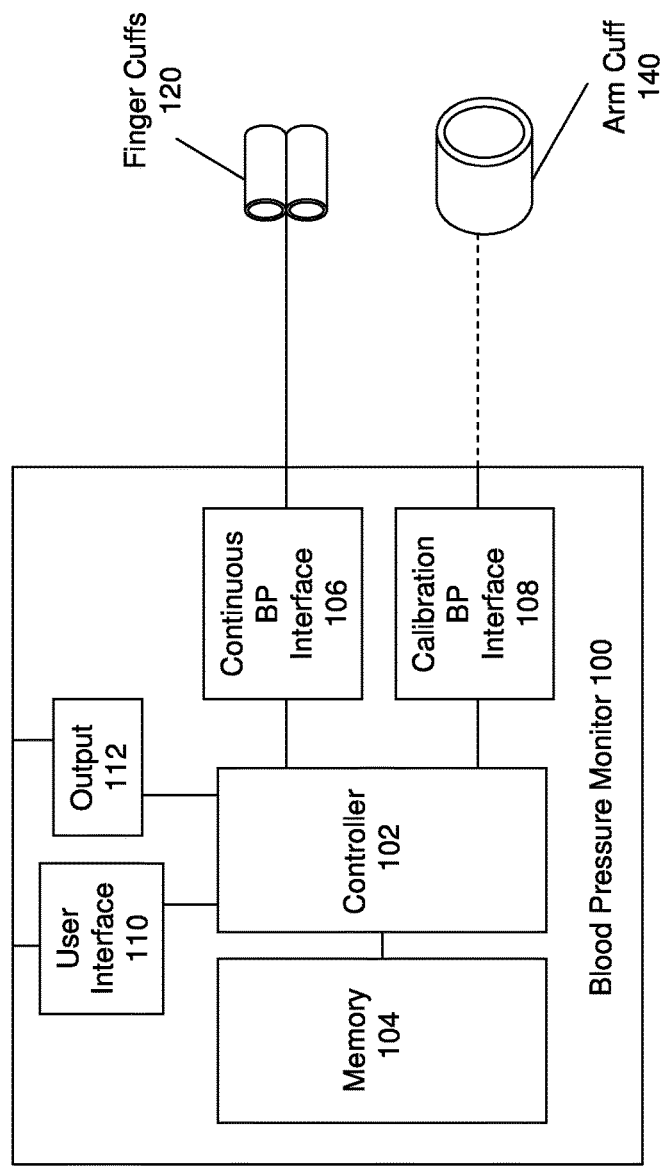
FIG. 1 shows a system for continuously measuring blood pressure and automatically recalibrating, in accordance with an embodiment of the present invention.

FIG. 1 shows a system for continuously monitoring blood pressure and automatically recalibrating, in accordance with an embodiment of the present invention. Blood pressure monitor 100 is connected via continuous BP interface 106 to a set of finger cuffs 120 (only one of which is used at any one time) to receive a continuous blood pressure signal, and via calibration BP interface 108 to arm cuff 140 to receive a calibration blood pressure signal when requested. Interfaces 106 and 108 are connected to controller 102 which may calculate a calibrated continuous blood pressure signal based on the blood pressure signals received from finger cuffs 120 and arm cuff 140 through interfaces 106 and 108. The controller executes its functions based on executable software code stored in memory 104. The controller 102 analyses the calibrated continuous blood pressure signal and issues instructions to the arm cuff blood pressure measurement device 140 to take a calibration blood pressure measurement when a threshold associated with the calibrated continuous blood pressure signal exceeds a predetermined threshold (as discussed with reference to FIG. 2). The controller 102 may issue an instruction for the arm cuff 140 to take a calibration blood pressure measurement at other times, such as at the start of a continuous blood pressure measurement or when requested by the user via user interface 110. Blood pressure signals may be stored in the memory 104 for future analysis and patient records.

The calibration blood pressure signal is analysed by the controller 102 and used to calculate a calibration function. The calibration function is applied by the controller 102 to the continuous blood pressure signal to calculate a calibrated blood pressure signal. The calibrated blood pressure signal may then be output via output 112. The output 112 may be a monitor, a network connection, a memory device or any other output.

The finger cuffs 120 may be such as those disclosed in U.S. patents U.S. Pat. No. 6,669,648 and U.S. Pat. No. 7,390,301 and US patent application US 2012/0059233. Two finger cuffs 120 are provided which may measure the blood pressure in two fingers. One finger is measured at a time and the measurements are periodically swapped between each finger in order to reduce the discomfort and stress applied to the fingers. Upon changeover, the new finger measurements are, in the embodiment, calibrated against the last continuous blood pressure values without any arm cuff measurements being taken.

The finger cuffs 120 may be located on the arm opposite to the arm carrying the arm cuff 140 to avoid an activation of the arm cuff 140 interrupting a measurement using a finger cuff 120. Alternatively, the arm 140 and finger cuffs 120 may be located on the same arm to allow the other arm to be free for other uses during the medical procedure. It should be noted that other means of continuously measuring blood pressure and of providing a calibration blood pressure signal may be used and that the present invention is not limited to working in conjunction with finger and arm cuffs.

Figure 2:
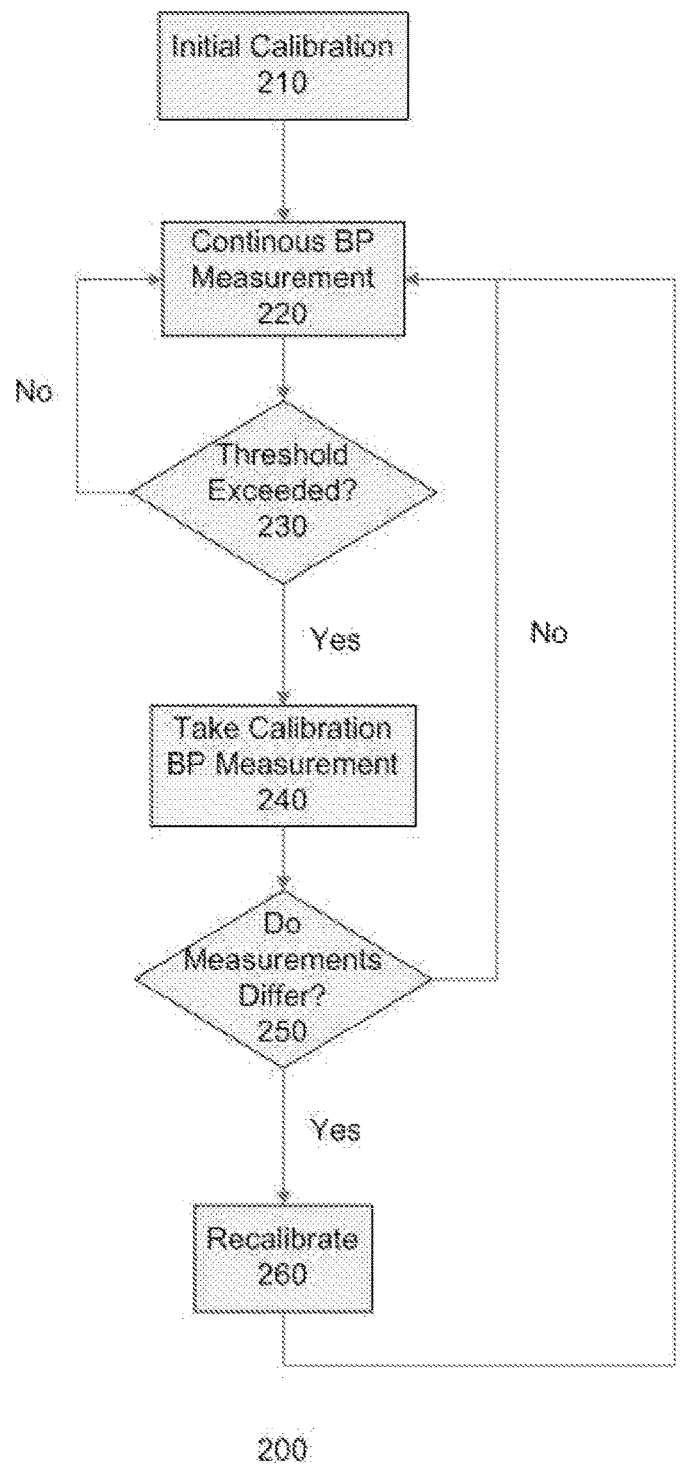
FIG. 2 shows a flowchart detailing a method for determining whether it is desirable to check the calibration of a monitored blood pressure signal.

FIG. 2 shows a flowchart detailing a method 200 for determining whether a continuous blood pressure signal requires recalibration, in accordance with an embodiment of the present invention. The method may be implemented by the apparatus described above.

Before measurements are recorded the continuous blood pressure signal is initially calibrated 210 using a calibration blood pressure signal. The continuous blood pressure signal and calibration blood pressure signal may, for example, be obtained using the finger cuffs 120 and arm cuff 140 shown in FIG. 1 respectively. Using arm cuffs for calibration measurements is preferred as such measurements at present are considered the gold standard. Once the blood pressure signal has been calibrated, calibrated continuous blood pressure measurements may be taken 220. The calibrated blood pressure signal is continuously monitored to check whether one or more preselected threshold values have been exceeded 230. If one of the threshold values is exceeded, then a new calibration blood pressure measurement is taken 240. If the calibrated continuous blood pressure measurement signal differs from the calibration signal by a predetermined amount, then the continuous blood pressure signal is recalibrated 260. If the calibrated continuous blood pressure signal does not differ from the calibration signal then no calibration is required and measurement 220 is continued. It will be appreciated that step 250 may be omitted so that the continuous blood pressure signal is recalibrated whenever the threshold in step 230 is exceeded. Once the continuous blood pressure signal is recalibrated 260, calibrated continuous blood pressure measurements are continued 220. By continuously monitoring the blood pressure measurements and recalibrating whenever threshold values are exceeded, the number of calibration measurements may be limited whilst still ensuring the accuracy of the measurements.

Figure 3A:
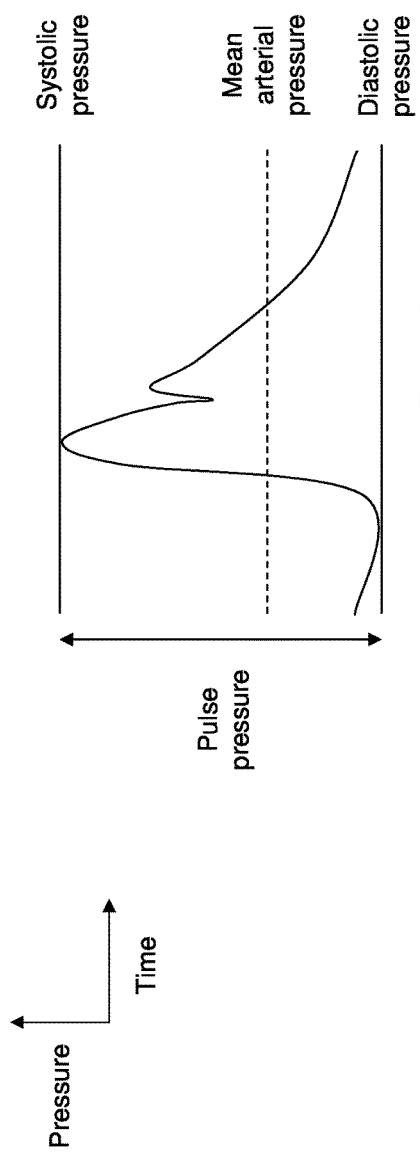
FIG. 3A illustrates the definition of pulse pressure.

FIG. 3A shows typical blood pressure variations over a cardiac cycle. The ordinate displays blood pressure, whilst the abscissa shows time. The maximum pressure over one cardiac cycle is the systolic pressure ($P_{sys}$) whilst the minimum pressure is the diastolic pressure ($P_{dia}$). The average pressure over one cardiac cycle is the mean arterial pressure (MAP). The difference between the systolic ($P_{sys}$) and diastolic ($P_{dia}$) pressure is the pulse pressure (PP):

$$PP = P_{sys} - P_{dia}$$

It has been found that deviations in pulse pressure from expected patterns provide a good indication that the calibration of blood pressure measurements should be checked. In particular, it was found that, if the pulse pressure falls outside of a predetermined pressure range this could indicate that the blood pressure measurements are no longer accurate. A drop of pulse pressure to below about 15 mmHG or a rise of pulse pressure to above about 150 mmHG were, for example, found to occur sufficiently rarely in normal physiology that they can reliably be considered to indicate misscalibration and can consequently be taken as an indicator that the calibration of the measurement should be checked.

Additionally, it was found that a rapid change in pulse pressure may indicate that the calibration of the measurement may no longer be correct. The embodiment therefore uses a rate of change in pulse pressure as an additional or alternative trigger for checking the calibration of the blood pressure measurements. An arm cuff measurement for checking the calibration is in particular triggered if the pulse pressure decreases by more than 50% within 90 seconds or increases by more than 100% within 90 seconds. While this trigger event uses a predetermined fixed time period for assessing the rate of change of pulse pressure an alternative or additional way of assessing the rate of change is to consider the amount of change in pulse pressure from a set/defined point in time onwards. A large change in pulse pressure since the last calibration or calibration check, for example, may indicate that a check of the current calibration is required. In the embodiment the signal is recalibrated if the pulse pressure decreases by more than 60% since the last calibration or calibration check or increases by more than 150% since the last calibration or calibration check.

A further parameter which was found to be a reliable indicator of mis-calibration is the med-dia ratio, that is the difference between the mean arterial pressure (MAP) and the diastolic pressure ($P_{dia}$) divided by the pulse pressure (PP), i.e.:

$$MD = \frac{MAP - P_{dia}}{P_{sys} - P_{dia}}$$

The med-dia ratio is approximately ⅓ under normal conditions as, at normal resting rates MAP can be approximated as:

$$MAP \approx \frac{1}{3} P_{sys} + \frac{2}{3} P_{dia}$$

It has been found that a check of the calibration may be required if the med-dia ratio falls outside a predetermined band. In particular med-dia ratios of less than 21% (0.21) or more than 51% (0.51) have been identified as reliable triggers for calibration checks.

In order to filter out short-term fluctuations, a moving average may be applied to the parameters measured, such as pulse pressure and med-dia-ratio. This should improve the signal to noise ratio, allowing for a clearer blood pressure signal, and ensure that noise or short-term miscalibrations do not cause initiation of a calibration check or recalibration. A further method of filtering such noise or short-term miscalibrations is a median filter applied to the parameters measured, where the median of the moving window is use instead of the moving average.

Once a threshold has been exceeded, a calibration measurement is taken. This may be used to calibrate the continuous blood pressure signal; however, in order to maintain consistency of measurements, it may be beneficial to only recalibrate the calibrated continuous blood pressure signal if it differs from the calibration measurement by a predetermined amount. It has been found that calibration may be required if either the systolic or diastolic pressures of the calibrated signal differ from those measured in the calibration signal by 13 mmHG.

In the embodiment the user is free to request re-calibration or a swap between finger cuffs used at any time. Where the user requests a calibration measurement, or where the user requests the finger cuff measurements to swap to the other finger, recalibration is performed regardless of the difference between the calibrated and calibration signals.

If a calibration measurement does not differ sufficiently from the calibrated blood pressure measurement, then the system is likely to be calibrated correctly, and the device inhibits automatic re-calibration for a predetermined period, for example for five minutes in an embodiment. Furthermore, if a calibration check is initiated as a result of an absolute value exceeding a threshold, such as maximum pulse pressure, and no recalibration is required, then the threshold may be disregarded for a period afterwards, such as until the source of the blood pressure signal is next changed/finger cuffs are next swapped between fingers.

Calibration measurements may also be taken between finger changes. In an embodiment a calibration measurement may, for example, be taken if the time elapsed since the last finger change or since the last calibration measurement is longer than four minutes. If a calibration measurement is being taken then any timed finger change may be delayed.

Figure 3B:
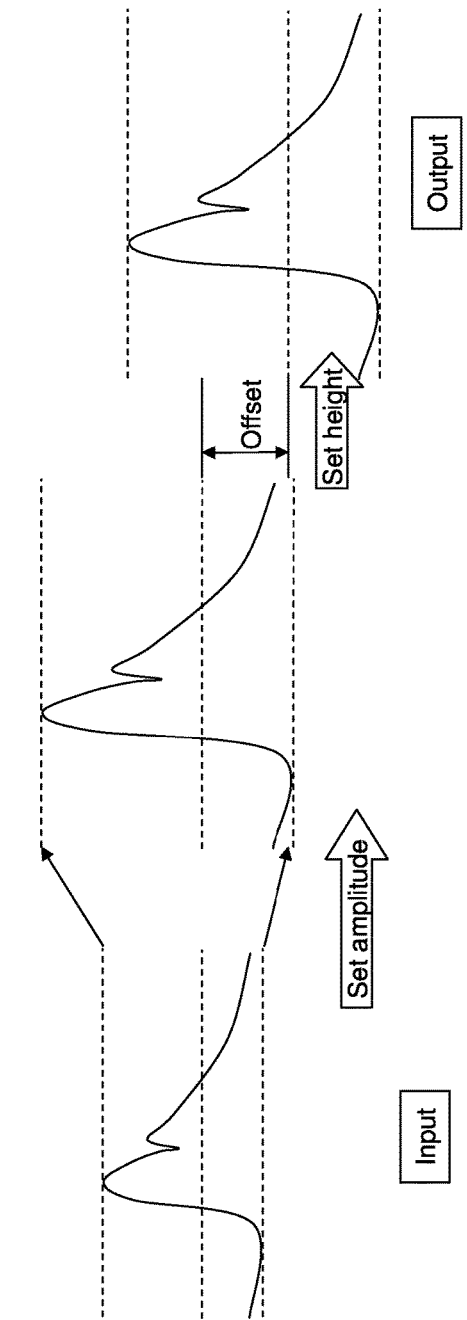
FIG. 3B illustrates the calibration of a blood pressure measurement.

FIG. 3B shows how a calibrated blood pressure signal may be calculated based on an input blood pressure signal and a second calibration blood pressure signal. The input blood pressure signal is amplified such that it has the same amplitude, or pulse pressure, as the calibration signal. This amplified blood pressure signal is offset by a bias pressure so that the mean arterial pressure is matched to the calibration signal. The final calibrated measurement should therefore have similar systolic and diastolic pressures to the calibration signal. It should be noted that calibration may involve only matching one of the pulse pressure or the mean arterial pressure. Equally, other factors may be used to calibrate the input signal. To more accurately calibrate an input continuous blood pressure signal, the average values over multiple cardiac cycles may be used, for instance, the last ten beats recorded in the continuous blood pressure signal.

The factors calculated from the calibration signal are used to form a calibration function which is continuously applied to the input continuous blood pressure signal from the time of calibration onwards. When each recalibration is performed, a new calibration function is calculated and applied to the continuous blood pressure signal to provide a calibrated continuous blood pressure measurement.

While certain embodiments have been described, the embodiments have been presented by way of example only, an area not intended to limit the scope of the inventions. Indeed, the novel methods, apparatus and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A device for use in monitoring blood pressure, the device being configured to be communicatively connected to a first blood pressure measurement device and to a second blood pressure measurement device, the device comprising a controller configured to:
    continuously monitor a first blood pressure measurement based on a first blood pressure signal received from the first blood pressure measurement device;
    calculate a pulse pressure value using the first blood pressure signal only;
    initiate acquiring a calibration blood pressure signal from the second blood pressure measurement device and a calibration blood pressure measurement based on the calibration blood pressure signal in response to at least one of the following conditions being satisfied: (1) the pulse pressure value exceeds a predetermined threshold, or (2) a change in pulse pressure over a period of time exceeds a predetermined threshold; and
    re-calibrate the first blood pressure measurement based on the calibration blood pressure measurement in response to the first blood pressure measurement differing from the calibration blood pressure measurement by more than a predetermined amount, wherein the re-calibration comprises amplifying the first blood pressure signal and/or applying an offset to the first blood pressure signal so that a systolic pressure and a diastolic pressure of the first blood pressure signal matches, respectively, a systolic pressure and a diastolic pressure of the calibration blood pressure signal.

2. The device according to claim 1, wherein the controller is configured to inhibit initiating acquiring a calibration blood pressure measurement if a calibration blood pressure measurement has been taken during a predetermined preceding period of time and if the first blood pressure measurement was not recalibrated in view of the calibration blood pressure measurement.

3. The device according to claim 1, wherein the controller is further configured to inhibit initiating acquiring a calibration blood pressure measurement based on a specific predetermined pulse pressure threshold being exceeded, if, during a predetermined preceding period of time, a calibration blood pressure measurement has been taken based on said predetermined pulse pressure threshold being exceeded and the first blood pressure measurement was not recalibrated.

4. The device according to claim 1, further comprising an arm cuff or a finger cuff.

5. A device for use in monitoring blood pressure, the device being configured to be communicatively connected to a first blood pressure measurement device and to a second blood pressure measurement device, the device comprising a controller configured to:

continuously monitor a first blood pressure measurement based on a first blood pressure signal received from the first blood pressure measurement device;

calculate a pulse pressure value using the first blood pressure signal only;

initiate acquiring a calibration blood pressure signal from the second blood pressure measurement device and a calibration blood pressure measurement based on the calibration blood pressure signal in response to at least one of the following conditions being satisfied: (1) the pulse pressure value is less than 15 mmHg, or (2) the pulse pressure value exceeds 150 mmHg; and re-calibrate the first blood pressure measurement based on the calibration blood pressure measurement in response to the first blood pressure measurement differing from the calibration blood pressure measurement by more than a predetermined amount, wherein the re-calibration comprises amplifying the first blood pressure signal and/or applying an offset to the first blood pressure signal so that a systolic pressure and a diastolic pressure of the first blood pressure signal matches, respectively, a systolic pressure and a diastolic pressure of the calibration blood pressure signal.

6. A device for use in monitoring blood pressure, the device being configured to be communicatively connected to a first blood pressure measurement device and to a second blood pressure measurement device, the device comprising a controller configured to:

continuously monitor a first blood pressure measurement based on a first blood pressure signal received from the first blood pressure measurement device;

calculate a pulse pressure value using the first blood pressure signal only;

initiate acquiring a calibration blood pressure signal from the second blood pressure measurement device and a calibration blood pressure measurement based on the calibration blood pressure signal in response to a change in pulse pressure over a period of time exceeding a predetermined threshold; and re-calibrate the first blood pressure measurement based on the calibration blood pressure measurement in response to the first blood pressure measurement differing from the calibration blood pressure measurement by more than a predetermined amount, wherein the re-calibration comprises amplifying the first blood pressure signal and/or applying an offset to the first blood pressure signal so that a systolic pressure and a diastolic pressure of the first blood pressure signal matches, respectively, a systolic pressure and a diastolic pressure of the calibration blood pressure signal.

7. The device according to claim 6, wherein the period of time is a fixed time period.

8. The device according to claim 7, wherein the acquisition of the calibration blood pressure measurement is initiated in response to the pulse pressure decreasing by more than 50 percent over the period of time or in response to the pulse pressure increasing by more than 100 percent over the period of time.

9. The device according to claim 8, wherein the period of time is 90 seconds.

* * * * *